United States Patent [19]
Krape et al.

[11] Patent Number: 5,955,475
[45] Date of Patent: Sep. 21, 1999

[54] PROCESS FOR MANUFACTURING PAROXETINE SOLID DISPERSIONS

[75] Inventors: Philip J. Krape, Wilmington, Del.; Sou-Chan Chang, Westbury, N.Y.; William A. Hein, II, Hasbrouck Heights, N.J.; Christopher A. Teleha, Bear, Del.

[73] Assignee: Endo Pharmaceuticals Inc., Chadds Ford, Pa.

[21] Appl. No.: 08/885,068

[22] Filed: Jun. 30, 1997

[51] Int. Cl.$^6$ ................................................. A61K 31/445
[52] U.S. Cl. ............................................. 514/321; 514/937
[58] Field of Search ............................................. 514/321

[56] References Cited

U.S. PATENT DOCUMENTS

| | | | |
|---|---|---|---|
| 4,007,146 | 2/1977 | Christuensen et al. | 260/293.58 |
| 4,721,723 | 1/1988 | Barnes et al. | 514/321 |
| 4,933,360 | 6/1990 | Pandit et al. | 514/417 |

FOREIGN PATENT DOCUMENTS

| | | | |
|---|---|---|---|
| WO 9515155 A1 | 6/1995 | WIPO. | |
| WO 9516448 A1 | 6/1995 | WIPO. | |
| WO 9631197 A1 | 10/1996 | WIPO. | |

*Primary Examiner*—Leonard Schenkman
*Attorney, Agent, or Firm*—Schnader Harrison Segal & Lewis LLP; Michael B. Fein

[57] ABSTRACT

Solid dispersions of poorly soluble drugs are disclosed which are prepared using a solvent or fusion process. Such dispersions are manufactured with the free base of the drug, specifically paroxetine free base, an oil, allowing for a low temperature for the fusion process, decreased organic solvent volumes for the solvent process and the formation of a paroxetine salt during the solid dispersion manufacture process.

27 Claims, No Drawings

PROCESS FOR MANUFACTURING PAROXETINE SOLID DISPERSIONS

FIELD OF THE INVENTION

The present invention relates to the field of solid dispersions of poorly water soluble drugs, to processes for their preparation and their use in pharmaceutical compositions. Specifically, the present invention relates to solid dispersions resulting from fusion or solvent methods for the incorporation of poorly water soluble drugs into pharmaceutically acceptable carriers. More specifically, the invention relates to the solid dispersions of paroxetine, processes for the preparation of such solid dispersions, pharmaceutical compositions containing the same and their use thereof in therapy.

BACKGROUND

The compound (−)-trans-4-((4'-fluorophenyl)3-(3'4'-methylenedioxyphenoxymethyl)-piperidine, commonly known as paroxetine, is a viscous oil and poorly water soluble drug with a commercial need for useful pharmaceutical compositions. A solid dispersion of paroxetine or its acid addition salt, never described before now in the literature, would provide a solid product on a commercial scale with good handling qualities and physiological acceptability without the need or expense to manufacture crystalline materials.

Pharmaceutical compositions with good dissolution and bioavailability can be formulated from solid dispersions of pharmaceutically active ingredients. Advantages claimed for pharmaceutical solid dispersions include potential use in controlled release formulations, stabilizing the drug from polymorphic conversions, improving poor handling properties of drug substances and protecting certain drugs against decomposition during administration. Solid dispersions of pharmaceutically active ingredients can be formed from a number of pharmaceutically acceptable carriers. U.S. Pat. No. 4,933,360 describes a novel process and product comprising chlorthalidone as the pharmaceutical active ingredient and polyvinylpyrrolidone (PVP) as the pharmaceutically acceptable carrier. The techniques have been described in general by W. L. Chiou et al., J. Pharm. Sci. 60(28)(1971) and S. Riegelman et al, U.S. Pat. No. 4,151,273. As defined in the Chiou article the term "solid state dispersion" means a dispersion of one or more active ingredients in an inert carrier or matrix in a solid state prepared by a melting (fusion), solvent, or combined melt-solvent method. The dispersion of an active ingredient in a solid carrier or diluent by traditional mechanical mixing is not included within the definition of this term.

In the "solvent method", the active ingredient is conventionally dispersed in a water soluble carrier by dissolving a physical mixture containing the active ingredient and the pharmaceutically acceptable carrier in a common organic solvent and then removing the solvent by evaporation. The resulting solid dispersion is recovered and used in the preparation of suitable pharmaceutical compositions formulated using conventional methods.

Manufacture of solid dispersions by the fusion or "melt" process involves combination of the pharmaceutically acceptable carrier and the poorly water soluble drug where the two components are allowed to melt at temperatures at or above the melting point of both the drug and the carrier. In the fusion process, the drug and carrier are first physically mixed and then both are melted. The molten mixture is then cooled rapidly to provide a congealed mass which is subsequently milled to produce a powder. Spray-congealing techniques used to produce pellets have been described by Kanig (J. Pharm. Sci. 53, 188 (1964)) for dispersions containing mannitol and by Kreuschner et al. (Acta Pharm. Tech. 26, 159 (1980)) for phenylbutazone-urea.

In general, problems which can be associated with known melting (fusion), solvent, melt solvent, and coprecipitation techniques can include excess solvent usage, identifying carrier/drug combinations that can be conveniently melted (fused) or codissolved, the use of heat to effect solution or fusion which may result in decomposition of the drug and/or carrier, and identifying conditions and properties effecting coprecipitation. Salts of drugs may present particular problems with identifying organic solvents or solvents capable of dissolving both the drug and a pharmaceutically acceptable carrier.

U.S. Pat. No. 4,007,196 discloses paroxetine as an inhibitor of 5-hydroxytryptamine (5HT) uptake and thus of therapeutic use as an anti-depressant. Paroxetine is well known and widely marketed as a medicinal agent. As disclosed in U.S. Pat. No. 4,007,196, paroxetine is obtained as the free base and then converted to its maleate salt. However, paroxetine is a poorly water soluble drug and difficult to formulate into useful pharmaceutical compositions.

U.S. Pat. No. 4,721,723 indicates that because of its basicity, it is preferred that paroxetine be used as a therapeutic agent in the form of an acid addition salt. The free base is a viscous oil which is difficult to handle and formulate into a finished dosage form for therapeutic use. As such, U.S. Pat. No. 4,721,723 further discloses crystalline paroxetine hydrochloride hemihydrate as a novel material with better handling properties than anhydrous paroxetine hydrochloride which is an hygroscopic solid with poor handling properties.

In general, the hydrochloride salt of a basic compound is preferred for therapeutic use because of its physiological acceptability. Additionally, a pharmaceutically active ingredient should not contain appreciable amounts of bound or unbound organic solvent. Once the salt has been formed, it must be isolated from solvents by filtration or other means in order for the paroxetine salt to be conveniently formulated into a pharmaceutical composition. Many solvents, including water, form solvates or clathrates of paroxetine hydrochloride wherein the solvent cannot be removed by conventional drying techniques such as vacuum oven drying. U.S. Pat. No. 4,721,723 discloses the hemihydrate solvate form of paroxetine hydrochloride while International Publication Number WO 96/24595 discloses paroxetine hydrochloride solvates other than the propan-2-ol solvate as precursors in the preparation of paroxetine hydrochloride substantially free of bound organic solvent. Additionally, International Publication Number WO 96/24595 also discloses four novel paroxetine hydrochloride anhydrates substantially free of bound solvent. However, none of the above publications specifically describe the stability or hygroscopicity of non-crystalline anhydrates of paroxetine hydrochloride in a solid dispersion.

The present invention relates to novel processes for incorporating paroxetine, a poorly water soluble drug, into a solid dispersion and its use in pharmaceutical compositions containing the same.

It has now been surprisingly found that solid dispersions of anhydrous paroxetine hydrochloride can be manufactured by a fusion process using the free base of paroxetine, and dry hydrogen chloride gas at temperatures substantially lower then the melting point of paroxetine hydrochloride using a pharmaceutically acceptable carrier with a melting point significantly lower than that of anhydrous paroxetine hydrochloride. The resulting solid dispersion is substantially free of organic solvent, is anhydrous and has improved handling properties.

Furthermore, it has been found that solid dispersions of anhydrous paroxetine salts, preferably the hydrochloric acid salt, can be manufactured by a novel solvent process using a pharmaceutically acceptable carrier, paroxetine free base, a non-aqueous solvent and a solution or gas of the acid addition salt.

The manufacturing of noncrystalline anhydrates of paroxetine hydrochloride in a solid dispersion improves the formulating of paroxetine free base, provides a solid which is readily formulated into a commercial dosage form, eliminates the additional steps to manufacture crystalline material for handling purposes and presumptively reduces manufacturing costs associated with those steps.

SUMMARY OF THE INVENTION

Solid dispersions of poorly soluble drugs are disclosed which are prepared using a solvent or fusion process. Such dispersions are manufactured with the free base of the drug, specifically paroxetine free base, an oil, allowing for a low temperature for the fusion process, decreased organic solvent volumes for the solvent process and the formation of a paroxetine salt during the solid dispersion manufacture process.

DETAILED DESCRIPTION OF THE INVENTION

In a first embodiment the invention provides a process for preparing a water soluble solid state dispersion of paroxetine and a pharmaceutically acceptable polymeric carrier, which process comprises:

(a) forming a solution of a water soluble pharmaceutically acceptable polymeric carrier and a non-aqueous solvent, (b) dissolving paroxetine free base into the solution, wherein the ratio by weight of water soluble pharmaceutically acceptable polymeric carrier to paroxetine is in the range of about 4:1 to about 1:1;

(c) contacting the paroxetine free base in solution with at least one equivalent of an acid, wherein the acid is a non-toxic inorganic or organic acid, to form a pharmaceutically acceptable paroxetine salt in solution; and (d) removing the non-aqueous solvent by evaporation under vacuum.

In a preferred embodiment the invention provides a process for preparing a water soluble solid state dispersion wherein the polymeric carrier is polyethylene glycol or polyvinylpyrrolidone.

In a more preferred embodiment the invention provides a process for preparing a water soluble solid state dispersion of paroxetine and a pharmaceutically acceptable polymeric carrier, which process comprises:

(a) forming a solution of polyethylene glycol and ethanol, (b) dissolving paroxetine free base into the solution, wherein the ratio by weight of polyethylene glycol to paroxetine is in the range of about 4:1 to about 1:1;

(c) contacting the paroxetine free base in solution with at least one equivalent of dry hydrogen chloride, wherein the dry hydrogen chloride is dissolved in methanol or ethanol, to form pharmaceutically acceptable paroxetine hydrogen chloride in solution; and (d) removing the non-aqueous solvent by evaporation under vacuum.

In an even more preferred embodiment the invention provides a process for preparing a water soluble solid state dispersion of paroxetine and a pharmaceutically acceptable polymeric carrier, which process comprises:

(a) forming a solution of polyvinylpyrrolidone and ethanol, (b) dissolving paroxetine free base into the solution, wherein the ratio by weight of polyvinylpyrrolidone to paroxetine is in the range of about 4:1 to about 1:1;

(c) contacting the paroxetine free base in solution with at least one equivalent of dry hydrogen chloride, wherein the dry hydrogen chloride is dissolved in methanol or ethanol, to form pharmaceutically acceptable paroxetine hydrogen chloride in solution; and (d) removing the non-aqueous solvent by evaporation under vacuum.

In a second embodiment the invention provides a process for preparing a water soluble solid state dispersion of paroxetine and a pharmaceutically acceptable polymeric carrier, which process comprises:

(a) contacting a water soluble pharmaceutically acceptable polymeric carrier with paroxetine free base to form an intimate mixture, wherein the ratio by weight of water soluble pharmaceutically acceptable polymeric carrier to paroxetine free base is in the range of about 4:1 to about 1:1 ;

(b) heating the mixture to form a molten homogeneous melt of polymeric carrier and paroxetine free base;

(c) contacting the molten homogeneous melt of polymeric carrier and paroxetine free base with at least one equivalent of dry hydrogen chloride to form pharmaceutically acceptable paroxetine hydrogen chloride in the molten homogeneous melt; and (d) cooling the molten homogeneous melt to form a water soluble solid state dispersion.

In a preferred second embodiment the invention provides a process for preparing a water soluble solid state dispersion of paroxetine and a pharmaceutically acceptable polymeric carrier, which process comprises:

(a) contacting a polyethylene glycol with paroxetine free base to form an intimate mixture, wherein the ratio by weight of polyethylene glycol to paroxetine free base is in the range of about 4:1 to about 1:1;

(b) heating the mixture to form a molten homogeneous melt of polyethylene glycol and paroxetine free base;

(c) contacting the molten homogeneous melt of polyethylene glycol and paroxetine free base with at least one equivalent of dry hydrogen chloride to form pharmaceutically acceptable paroxetine hydrogen chloride in the molten homogeneous melt; and (d) cooling the molten homogeneous melt to form a water soluble solid state dispersion.

In a third embodiment the invention provides a solid state dispersion comprising a pharmaceutically acceptable polymeric carrier and paroxetine.

In a fourth embodiment the invention provides for a pharmaceutical composition comprising one or more pharmaceutically acceptable excipients and a solid state dispersion comprising paroxetine and a pharmaceutically acceptable polymeric carrier.

In a fifth embodiment the invention provides for a method of treating depression in a warm-blooded animal comprising administering to said animal a solid state dispersion, comprising paroxetine and a pharmaceutically acceptable polymeric carrier, the amount of paroxetine hydrochloride in said dispersion being effective for treating depression.

By "paroxetine" it is meant the generic name for the compound described in Example 2 of U.S. Pat. No. 4,007,196, also known as (−)-trans-4-(4'-fluorophenyl)-3-(3',4'-methylenedioxyphenoxymethyl)-piperidine, and pharmaceutically acceptable salts thereof. Therefore, as used herein, the term paroxetine refers to "paroxetine free base" or "paroxetine salt". The term "paroxetine free base", or simply "free base", specifically refers to paroxetine as a material which is a viscous oil at standard temperature and pressure. The term "paroxetine salt" is used to describe an acid addition product of paroxetine. For example, in the case of the hydrogen chloride, the acid addition product is called "paroxetine hydrochloride" or simply "hydrochloride salt."

The compound paroxetine herein described has two asymmetric centers. Unless otherwise indicated, the (−)-trans isomer is the preferred enantiomer. However, all chiral, diastereomeric and racemic forms are included in the present invention. It is well known in the art how to prepare optically active forms, such as by resolution of racemic forms or by synthesis, from optically active starting materials. Use of all chiral, diastereomeric, racemic forms are intended, unless the specific stereochemistry or isomer form is specifically indicated.

As used herein, the term "non-aqueous solvent" refers to any of the following: methanol, ethanol, n-propanol, i-propanol, n-butanol, i-butanol, s-butanol, toluene, benzene, supercritical liquid $CO_2$, chloroform, methylene chloride, acetonitrile, ketones (for example, but not limited to, dimethylketone, methylethylketone, and diethylketone), dimethylformamide, dimethylsulfoxide, esters (for example, but not limited to, ethyl acetate), ethers (for example, but not limited to, diethylether and dipropylether), 1,4-dioxane, tetrahydrofuran, pentanes, hexanes, heptanes, trichloroethene, or suitable mixtures of thereof.

Preferably the solvent should be (a) capable of dissolving both the active ingredient and the carrier, (b) chemically inert with respect to the active ingredient and the carrier, and (c) sufficiently volatile to permit removal by evaporation using conventional techniques. Alkanols having from one to four carbon atoms would in general be expected to be useful for preparing solid state dispersions by the solvent method. In the present invention additional characteristics have been found to be important. The organic solvent should be (d) capable of dissolving both the free base and the pharmaceutically acceptable salt of the active ingredient; (e) chemically inert with respect to both the free base of the active ingredient and the salt formed after reaction with the acidified organic solvent; and (f) capable of dissolving sufficient acid to permit complete or nearly complete conversion of the free base to the salt.

As used herein, the term "pharmaceutically acceptable polymeric carrier", or "polymeric carrier" refers to any of the following: hydroxypropyl cellulose, methyl cellulose, carboxymethyl cellulose, sodium carboxymethyl cellulose, cellulose acetate phthalate, cellulose acetate butyrate, hydroxyethyl cellulose, ethyl cellulose, polyvinyl alcohol, polypropylene, dextrans, dextrins, hydroxypropyl-beta-cyclodextrin, chitosan, co(lactic/glycolid) copolymers, poly (orthoester), poly(anhydrate), polyvinyl chloride, polyvinyl acetate, ethylene vinyl acetate, lectins, carbopols, silicon elastomers, polyacrylic polymers, maltodextrins, lactose, fructose, inositol, trehalose, maltose, raffinose, polyvinylpyrrolidone (PVP), polyethylene glycol (PEG), and alpha-, beta-, and gamma-cyclodextrins, or suitable mixtures of thereof.

In the present invention, additional characteristics have been found to be important. The pharmaceutically acceptable carrier should be (a) capable of being miscible with both the free base and the salt form of the drug substance, (b) capable of keeping the salt in a homogeneous noncrystalline solid state dispersion after the solvent has been removed by evaporation and (c) chemically inert with respect to the free base of the active ingredient, the salt of the free base, and the acidified organic solvent.

As used herein, the term "pharmaceutically acceptable salt" refers to derivatives of paroxetine wherein paroxetine is modified by making acid addition salts of the compound. Examples of pharmaceutically acceptable salts include, but are not limited to, mineral or organic acid salts of the basic piperidine residue; and the like. The pharmaceutically acceptable salts of paroxetine include conventional non-toxic salts or quaternary ammonium salts, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethanesulfonic, ethanedisulfonic, oxalic, isethionic, and the like.

The pharmaceutically acceptable salts of paroxetine can be prepared according to the method of the present invention would include introduction of or delivery of the acid moiety by various means. In the fusion method, the acidic moiety would be introduced in neat form. In the solution method, the acidic moiety could be introduced in neat form or by the non-aqueous solvent, which is later removed. Generally, the salts are prepared by reacting the free base with stoichiometric amounts or with an excess of the desired salt-forming inorganic or organic acid.

Lists of suitable salts are found in *Remington's Pharmaceutical Sciences*, 17th ed., Mack Publishing Company, Easton, PA, 1985, p. 1418, the disclosure of which is hereby incorporated by reference.

As used herein, the term "dry hydrogen chloride gas" refers to hydrogen chloride gas commercially available in cylinders containing compressed gas which is dried before use. Generally, dry hydrogen chloride gas is commercially prepared by bubbling hydrogen chloride gas through concentrated sulfuric acid or a comparable drying agent.

The disclosure of all references used herein are hereby incorporated by reference.

It is the object of the present invention to provide improved processes for the preparation of a water soluble solid dispersion of a poorly water soluble drug or drug combination prepared by a fusion and/or solvent process for producing solid dispersions. The methods of the present invention, by way of example, and without limitation, may be further understood by the following descriptive procedures.

The general method for preparation of a solid dispersion by the solvent process proceeds by (1) forming a solution comprising a pharmaceutically acceptable carrier and a non-aqueous solvent. A preferred polymeric carrier is selected from one or more of polyvinylpyrrolidone, hydroxypropylmethyl cellulose, hydroxypropyl cellulose, methyl cellulose, block co-polymers of ethylene oxide and propylene oxide, and polyethylene glycol, wherein a more preferred polymeric carrier is either polyethylene glycol (PEG) having an average molecular weight of from about 1,000 to about 20,000 or polyvinylpyrrolidone (PVP) having an average molecular weight of from about 2,500 to about 3,000,000. A most preferred polymeric carrier is polyvinylpyrrolidone having an average molecular weight of from about 10,000 to about 450,000. A preferred non-aqueous solvent is an alcohol selected from methanol, ethanol, n-propanol, iso-propanol, n-butanol, iso-butanol, and sec-butanol, wherein a more preferred solvent is either methanol or ethanol, wherein a most preferred solvent is ethanol. It is also preferred that the non-aqueous solvent be dry or anhydrous. In forming a solution of a polymeric carrier and a non-aqueous solvent it is understood that heating of the solution is allowable, but is not required, provided that the temperature does not result in decomposition or degradation of any materials.

Upon forming said solution the process proceeds by (2) dissolving the free base of a poorly water soluble drug in the solution thus formed. Heating is allowable as in step (1) but not required. It is understood that the addition of a poorly soluble drug is not limited to one drug but might encompass a combination of one or more drugs provided at least one drug is a poorly water soluble drug in the form of a free base. It is preferred that the poorly water soluble drug in the form of a free base is paroxetine. The ratio by weight of water soluble pharmaceutically acceptable polymeric carrier to paroxetine is in the range of about 5:1 to about 1:1; preferably about 4:1 to about 1:1; more preferably about 3:1 to about 1.5:1; most preferably about 2:1.

It is also understood that the order of addition for the polymeric carrier, the nonaqueous solvent and the free base of the poorly water soluble drug is interchangeable. For example, the free base drug could be dissolved into the non-aqueous solvent after which the polymeric carrier is added.

Upon dissolution of the free base drug the process proceeds by (3) converting the free base to a pharmaceutically acceptable preferably the free base salt, preferably the paroxetine salt, can be formed by addition of an inorganic or an organic acid which preferably is non-toxic and pharmaceutically acceptable. The acid is added either as a gas, a liquid or as a solid dissolved into a nonaqueous solvent. The preferred acid is dry hydrogen chloride and the molar quantity of acid added to the solution of paroxetine free base and carrier may either be in stoichiometric proportion to the paroxetine free base or be in excess of the molar quantity of the paroxetine free base, especially when added as a gas. For example, the preferred range of hydrogen chloride added is, but not limited to, from about 1.0 to about 1.8 times the molar quantity of paroxetine free base. Although dry hydrogen chloride is readily added as a gas the preferred method to add the hydrogen chloride is in the form of hydrogen chloride dissolved into a non-aqueous solvent, preferably hydrogen chloride saturated methanol or ethanol. It is understood that upon addition of the acid, the formed free base salt remains dissolved in solution with the polymeric carrier.

Lastly, upon formation of the free base salt, the process proceeds by (4) recovering the non-aqueous solvent to form a solid state dispersion of the free base salt in the polymeric carrier. Any method of removal of the non-aqueous solvent which renders a homogeneous solid state dispersion is intended, although preferred are methods of evaporation under vacuum. Preferred methods of evaporation under vacuum include rotoevaporation, static vacuum drying and the combination thereof. It is understood that one skilled in the art of pharmaceutical formulations can determine a reasonable temperature at which the non-aqueous solvent can be removed, provided the temperature is not so high as to cause degradation or decomposition of the materials; however, it is preferred that evaporation occurs at about 20° C. to about 50° C. It is also preferred that evaporation of the non-aqueous solvent renders a solid state dispersion which is homogeneous and substantially free of non-aqueous solvent. By substantially free it is meant that the solid state dispersion contains less than 20% by weight of residual non-aqueous solvent, preferably less than 10%, more preferably less then 5%, most preferably less then 1%.

The ratio of paroxetine free base to the pharmaceutically acceptable carrier can be varied over a wide range and depends on the concentration of paroxetine required in the pharmaceutical dosage form ultimately administered. However, the preferred range of paroxetine in the solid dispersion is about 16% to about 50% of the total solid dispersion weight, more preferable is about 20% to about 50%, even more preferable is about 25% to about 40%, most preferable is about 33% of the total dispersion weight.

Alternatively, the general method for preparation of a solid dispersion can proceed by a fusion process wherein a water soluble pharmaceutically acceptable polymeric carrier is mixed with a poorly water soluble drug, preferably paroxetine free base, or drug combination, to form an intimate mixture. The mixture is heated at or near the temperature of the highest melting point of either the pharmaceutically acceptable carrier or poorly water soluble drug or drug combination, thus forming a melt. A preferred polymeric carrier is polyethylene glycol. A preferred ratio by weight of water soluble pharmaceutically acceptable polymeric carrier to poorly water soluble drug is in the range of about 5:1 to about 1:1; preferably about 4:1 to about 1:1; more preferably about 3:1 to about 1.5:1; most preferably about 2:1.

It is understood that the addition of a poorly soluble drug is not limited to one drug but might encompass a combination of one or more drugs provided at least one drug is a poorly water soluble drug in the form of a free base. It is preferred that the poorly water soluble drug in the form of a free base is paroxetine.

Alternatively, the water soluble pharmaceutically acceptable polymeric carrier can be heated to molten condition upon which the poorly water soluble drug, as the free base, can be added to the molten carrier, thus forming a molten homogeneous melt.

Upon forming said molten homogeneous melt the process proceeds by (2) diffusing dry hydrogen chloride gas through the molten drug/carrier mixture to effect salt formation of the drug.

Lastly, upon formation of the free base salt, the process proceeds by (4) cooling the molten homogeneous melt by conventional methods to form a water soluble solid state dispersion.

The ratio of paroxetine free base to the pharmaceutically acceptable carrier can be varied over a wide range and depends on the concentration of paroxetine required in the pharmaceutical dosage form ultimately administered. However, the preferred range of paroxetine in the solid dispersion is about 16% to about 50% of the total solid dispersion weight, more preferable is about 20% to about 50%, even more preferable is about 25% to about 40%, most preferable is about 33% of the total dispersion weight.

Alternatively, the general method for preparation of a solid dispersion can proceed by a combination of the fusion method and the solvent method.

Specifically, the poorly water soluble drug is paroxetine; for the fusion process the preferred pharmaceutically acceptable carrier is polyethylene glycol; for the solvent process the preferred pharmaceutically acceptable carrier is polyvinylpyrrolidone or polyethylene glycol, the preferred solvent is ethanol, the preferred pharmaceutically acceptable salt is hydrogen chloride, the preferred method to add the hydrogen chloride is in the form of ethanolic hydrogen chloride and the preferred method to recover the solvent is by evaporation at about 20° C. to about 50° C. by a combination of evaporation and static vacuum drying.

The present invention also provides a pharmaceutical composition comprising pharmaceutically acceptable excipients and a solid state dispersion of paroxetine hydrochloride and pharmaceutically acceptable polymeric carrier. Examples of pharmaceutically acceptable excipients include diluents, binders, disintegrants, coloring agents, flavoring agents, lubricants and/or preservatives. The pharmaceutical composition may be formulated by conventional methods of admixture such as blending, filling, granulation and compressing. These agents may be utilized in conventional manner, for example in a manner similar to that already used clinically for anti-depressant agents.

The composition is usually presented as a unit dose composition containing from 1 to 200 mg, more usually from 5 to 100 mg, for example 10 to 50 mg such as 12.5, 20, 25, or 30 mg. Such composition is normally taken from 1 to 6 times daily, for example 2,3, or 4 times daily so that the total amount of active agent administered is within the range of 5 to 400 mg.

Preferred unit dosage forms include tablets or capsules.

The invention also provides for a method of treatment of depression in mammals including humans which method comprises administering an effective amount of pharmaceutically acceptable solid state dispersion of paroxetine hydrochloride.

The invention further provides a solid state dispersion of paroxetine hydrochloride for use in the treatment of depression.

The following examples illustrate the invention. Examples 1–16, show the preparation of solid state dispersions while Examples 17 and 18 show pharmaceutical compositions.

EXAMPLE 1
PEG-8000/Paroxetine Free-Base, 2:1 wt Basis; Fusion Method

To a 50 mL pear-shaped round bottom flask (equipped with a small magnetic stir bar, rubber septa and a glass pipette) was added PEG-8000 (2.009 g) and paroxetine free-base (0.75 g). The flask was immersed into a water bath, which was heated to a temperature to effect melting of the PEG. Once free-flowing, the glass pipette was carefully lowered below the level of the melt, and a stream of hydrogen chloride gas (dried through conc. sulfuric acid) was bubbled through the pipette for 30 minutes. Stirring was maintained during this process. After the gas introduction, the pipette and the stir bar were removed and the mixture was allowed to cool to room temperature overnight. The solidified product was carefully scraped from the flask. This material could be optionally ground/milled to a desirable particle size.

$^1$H NMR analysis (CDCl$_3$) were wholly consistent with a mixture of PEG and paroxetine hydrochloride, and shows the expected resonance for PEG (3.63, m) and the characteristic signal for paroxetine hydrochloride (2.03, br. d)

Elemental Analysis: Calcd. for 2.009 : 0.83 (wt. basis) PEG-8000 and paroxetine HCl: % C, 56.82; % H, 8.07; % N, 1.04; % Cl, 2.83. Found: % C, 56.71; % H, 8.28; % N, 1.00; % Cl, 3.44.

EXAMPLE 2
PEG-8000/Paroxetine Free-Base, 2:1 wt Basis; Solution Method

To a 200 mL round bottom flask (equipped with a small magnetic stir bar, rubber septa) was added PEG-8000 (10.0 g) and methanol (140 mL). Paroxetine free-base (4.994 g) was added and stirred about 5 minutes until completely dissolved.

In a separate procedure, methanolic HCl was prepared by bubbling gaseous HCl (9.81 g) into weighed solution of methanol (50 mL). This standard solution (0.196 g/mL) could be used for other experiments.

Methanolic HCl (5 ml), prepared above, was added to the 200 mL flask and stirring continued for 10 minutes. The stir-bar was removed, the flask was placed on a rotary evaporator and concentrated with a bath temperature at 35° C. Once a thick paste was obtained the flask was placed under static high pressure vacuum, which was continued 18 hours. On occasion, the material was scraped free from the sides of the flask to assist in the removal of residual volatiles. The product was scraped from the flask and could be ground/milled to an acceptable particle size.

$^1$H NMR analysis (CDCl$_3$) were wholly consistent with a mixture of PEG and paroxetine hydrochloride, and shows the expected resonance for PEG (3.63, m) and the characteristic signal for paroxetine hydrochloride (2.03, br. d). No residual methanol was detected.

Elemental Analysis: Calcd. for 10.000: 5.54 (wt. basis) PEG-8000 and paroxetine HCl: % C, 57.31; % H, 7.86; % N, 1.27; % Cl, 3.43. Found: % C, 57.31; % H, 8.07; % N, 1.21; % Cl, 4.38.

EXAMPLE 3
PEG-8000/Paroxetine Free-Base, 4:1 wt Basis, Solution Method

Using PEG-8000 (4.013 g) and paroxetine free-base (1.015 g), and methanolic HCl (1 mL of a 0.19 g/mL solution) and the method of Example 2, a solid dispersion of PEG/paroxetine hydrochloride 4:1 wt basis was prepared.

$^1$H NMR analysis (CDCl$_3$) were wholly consistent with a mixture of PEG and paroxetine hydrochloride, and shows the expected resonance for PEG-8000 (3.63, m) and the characteristic signal for paroxetine hydrochloride (2.03, br. d). No residual methanol was detected.

Elemental Analysis: Calcd. for 4.013:1.126 (wt. basis) PEG-8000 and paroxetine HCl: % C, 56.23; % H, 8.32; % N, 0.78; % Cl, 2.11. Found: % C, 56.11; % H, 8.60; % N, 0.72; % Cl, 2.63.

EXAMPLE 4
PEG-8000/Paroxetine Free-Base, 1:1 wt Basis, Solution Method using ethanolic HCl An ethanolic HCl solution was prepared by bubbling HCl gas (3.23 g) into a solution (50 mL) of absolute ethanol.

Using PEG-8000 (2.007 g) and paroxetine free-base (2.066 g), in a mixture of ethanol (15 mL) and methanol (8 mL), was added ethanolic HCl (3 mL) and the method of Example 2, a solid dispersion of PEG/paroxetine hydrochloride 1:1 wt basis was prepared.

$^1$H NMR analysis (CDCl$_3$) were wholly consistent with a mixture of PEG and paroxetine hydrochloride, and shows the expected resonance for PEG (3.63, m) and the characteristic signal for paroxetine hydrochloride (2.03, br. d). 5% residual ethanol (wt basis) was detected.

Elemental Analysis: Calcd. for 2.007:2.292 (wt. basis) PEG-8000 and paroxetine HCl: % C, 58.77; % H, 7.29; % N, 1.90; % Cl, 5.15. Found: % C, 59.18; % H, 7.72; % N, 1.98; % Cl, 4.95.

EXAMPLE 5
PVP 29/32K/Paroxetine Free-Base, 2:1 wt Basis, Solution Method

Using PVP 29/32K (2.077 g), paroxetine free-base (1.008 g), methanol (28 mL), methanolic HCl (1.0 mL of a 0.196 g/mL solution) and the method of Example 2, a solid dispersion of PVP/paroxetine hydrochloride, 2:1 wt basis, was prepared.

$^1$H NMR analysis (CDCl$_3$) were wholly consistent with a mixture of PVP and paroxetine hydrochloride, and shows the expected resonances for PVP (series of br. m 3.4–1.6) and the characteristic signal for paroxetine hydrochloride (2.03, br. d). 4% methanol (wt basis) was detected.

Elemental Analysis: Calcd. for 2.077:1.118 (wt. basis) PVP and paroxetine HCl: % C, 61.13; % H, 7.74; % N, 8.82; % Cl, 5.89. Found: % C, 62.49; % H, 7.63; % N, 9.12; % Cl, 6.33.

EXAMPLE 6
PEG-8000/Paroxetine Free-Base, 2:1 wt Basis; Solution Method

As in Example 2, using ethanol instead of methanol as solvent, ethanolic HCl (solution prepared in Example 4), PVP 29/32K /paroxetine free-base, 2.006:1.048 (wt basis).

$^1$H NMR analysis (CDCl$_3$) were wholly consistent with a mixture of PVP and paroxetine hydrochloride, and shows the expected resonances for PVP (series of br. m 3.4–1.6) and the characteristic signal for paroxetine hydrochloride (2.03, br. d). 14% ethanol (wt basis) was detected.

Elemental Analysis: Calcd. for 2.006:1.048:0.124 (wt. basis) PVP/paroxetine HCl/ HCl: % C, 59.96; % H, 7.23; % N, 8.59; % Cl, 7.07. Found: % C, 61.39; % H, 7.32; % N, 8.67; % Cl, 7.96.

Using the methods described above and modifications thereof the following additional examples could be prepared by one skilled in the art:

| Example | Excipient | Ratio[1] | HCl equivalent | Method[2] |
|---|---|---|---|---|
| 7 | PVP | 1/1 | 1.0 | Solution |
| 8 | PVP | 2/1 | 1.0 | Solution |
| 9 | PVP | 3/1 | 1.0 | Solution |
| 10 | PEG | 1/1 | 1.0 | Solution |
| 11 | PEG | 2/1 | 1.0 | Solution |
| 12 | PEG | 3/1 | 1.0 | Solution |
| 13 | PEG | 4/1 | 1.0 | Solution |
| 14 | PEG | 1/1 | excess | Fusion |
| 15 | PEG | 3/1 | excess | Fusion |
| 16 | PEG | 4/1 | excess | Fusion |

[1]Weight basis of Excipient to Paroxetine free-base
[2]See Example 2 for Solution Method, Example 1 for Fusion.

Dosage and Formulation

The method of this invention can be administered by any means that produces contact of the active agent with the agent's site of action, serotonin re-uptake inhibition, in the body of a mammal. They can be administered by any conventional means available for use in conjunction with pharmaceuticals, either as individual therapeutic agents or in a combination of therapeutic agents.

The dosage of the novel compounds of this invention administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to 10 milligrams per kilogram of body weight.

Dosage forms (compositions suitable for administration) contain from about 0.1 milligram to about 100 milligrams of active ingredient per unit. In these pharmaceutical compositions the active ingredient will ordinarily be present in an amount of about 0.5–50% by weight based on the total weight of the composition.

The active ingredient can be administered orally in solid dosage forms, such as capsules, tablets, and powders.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Suitable pharmaceutical excipients are described in *Remington's Pharmaceutical Sciences,* Mack Publishing Company, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 10 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil is prepared and injected by means of a positive displacement pump into gelatin to form soft gelatin capsules containing 10 milligrams of the active ingredient. The capsules are washed and dried.

Tablets

A large number of tablets are prepared by conventional procedures so that the dosage unit was 10 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

The following examples further illustrate a specific embodiment of the present invention, and is considered an illustrative, but not limiting, description of the invention.

EXAMPLE 17
A 20 mg paroxetine base (as the HCl salt) tablet using a solid dispersion as described in Example 8

| Ingredient | mg/tablet | gm/1000 tablet batch |
|---|---|---|
| Paroxetine HCl* | 22.21 | 22.21 |
| Polyvinylpyrrolidone* | 40.00 | 40.00 |
| Dibasic dicalcium phosphate dihydrate | 210.79 | 210.79 |
| Sodium Starch Glycolate | 24.00 | 24.00 |
| Magnesium Stearate | 3.00 | 3.00 |
| Total | 300 mg | 300 gm |

*Theoretical quantities for a solid dispersion of Paroxetine HCl and polyvinylpyrrolidone as described in Example #8.

Procedure: Mill the paroxetine HCl/polyvinylpyrrolidone solid dispersion by passing through a 20 mesh screen. Blend the milled solid dispersion with the dibasic dicalcium phosphate dihydrate, sodium starch glycolate and magnesium stearate. Compress tablets to a weight of 300 mg with a tablet hardness of approximately 17 Strong-Cobb Units.

EXAMPLE 18

A 20 mg Paroxetine Base (as the HCl Salt) Tablet using a Solid Dispersion as Described in Example 11

| Ingredient | mg/tablet | gm/1000 tablet batch |
|---|---|---|
| Paroxetine HCl* | 22.21 | 22.21 |
| Polyethylene glycol* | 40.00 | 40.00 |
| Dibasic dicalcium phosphate dihydrate | 210.79 | 210.79 |
| Sodium Starch Glycolate | 24.00 | 24.00 |
| Magnesium Stearate | 3.00 | 3.00 |
| Total | 300 mg | 300 gm |

*Theoretical quantities for a solid dispersion of Paroxetine HCl and polyethylene glycol as described in Example #11.

Procedure: Mill the paroxetine HCl/polyethylene glycol solid dispersion by passing through a 20 mesh screen. Blend the milled solid dispersion with the dibasic dicalcium phosphate dihydrate, sodium starch glycolate and magnesium stearate. Compress tablets to a weight of 300 mg with a tablet hardness of approximately 17 Strong-Cobb Units.

What is claimed is:

1. A process for preparing a water soluble solid state dispersion of paroxetine salt and a pharmaceutically acceptable polymeric carrier, which process comprises:

(a) forming a solution of a water soluble pharmaceutically acceptable polymeric carrier and a non-aqueous solvent, (b) dissolving paroxetine free base into the solution, wherein the ratio by weight of water soluble pharmaceutically acceptable polymeric carrier to paroxetine is in the range of about 4:1 to about 1:1;

(c) contacting the paroxetine free base in solution with at least one equivalent of an acid, wherein the acid is a non-toxic inorganic or organic acid, to form a pharmaceutically acceptable non-crystalline paroxetine salt anhydrate in solution; and (d) removing non-aqueous solvent by evaporation under vacuum.

2. The process of claim 1 wherein said polymeric carrier is selected from one or more of the following: polyvinylpyrrolidone, hydroxypropylmethyl cellulose, hydroxypropyl cellulose, methyl cellulose, block co-polymers of ethylene oxide and propylene oxide, and polyethylene glycol.

3. The process of claim 1 wherein paroxetine free base is dissolved into a non-aqueous solvent before the polymeric carrier is dissolved into the non-aqueous solvent.

4. The process of claim 1 wherein the non-aqueous solvent is an alcohol selected from methanol, ethanol, n-propanol, iso-propanol, n-butanol, iso-butanol, and sec-butanol.

5. The process of claim 1 wherein the non-aqueous solvent is ethanol.

6. The process of claim 1 wherein the acid is hydrogen chloride in the form of dry hydrogen chloride gas or dry hydrogen chloride dissolved into a non-aqueous solvent.

7. The process of claim 1 wherein said polymeric carrier is polyvinylpyrrolidone.

8. The process of claim 7 wherein the polymeric carrier is polyvinylpyrrolidone having an average molecular weight of from about 2,500 to about 3,000,000.

9. The process of claim 7 wherein the non-aqueous solvent is an alcohol selected from methanol, ethanol, n-propanol, iso-propanol, n-butanol, iso-butanol, and sec-butanol.

10. The process of claim 7 wherein the non-aqueous solvent is ethanol.

11. The process of claim 7 wherein the acid is hydrogen chloride in the form of dry hydrogen chloride gas or dry hydrogen chloride dissolved into a non-aqueous solvent.

12. The process of claim 7 wherein said solvent is ethanol, said acid is dry hydrogen chloride, and wherein the dry hydrogen chloride is dissolved in methanol or ethanol, to form pharmaceutically acceptable paroxetine hydrogen chloride in solution.

13. A solid state dispersion of a pharmaceutically acceptable polymeric carrier and noncrystalline paroxetine hydrochloride anhydrate produced by the process of claim 12.

14. The process of claim 1 wherein said polymeric carrier is polyethylene glycol and said acid is a non-toxic inorganic or organic acid.

15. The process of claim 14 wherein the polymeric carrier is polyethylene glycol having an average molecular weight of from about 1,000 to about 20,000.

16. The process of claim 14 wherein the non-aqueous solvent is an alcohol selected from methanol, ethanol, n-propanol, iso-propanol, n-butanol, iso-butanol, and sec-butanol.

17. The process of claim 14 wherein the non-aqueous solvent is ethanol.

18. The process of claim 14 wherein the acid is hydrogen chloride in the form of dry hydrogen chloride gas or dry hydrogen chloride dissolved into a non-aqueous solvent.

19. The process of claim 14 wherein said solvent comprises ethanol, said acid is dry hydrogen chloride, wherein the dry hydrogen chloride is dissolved in methanol or ethanol and said removing non-aqueous solvents comprises removing ethanol and, if present, methanol.

20. A solid state dispersion of a pharmaceutically acceptable polymeric carrier and noncrystalline paroxetine hydrochloride anhydrate produced by the process of claim 1.

21. A process for preparing a water soluble solid state dispersion of paroxetine and a pharmaceutically acceptable polymeric carrier, which process comprises:

(a) contacting a water soluble pharmaceutically acceptable polymeric carrier with paroxetine free base to form an intimate mixture, wherein the ratio by weight of water soluble pharmaceutically acceptable polymeric carrier to paroxetine free base is in the range of about 4:1 to about 1:1;

(b) heating the mixture to form a molten homogeneous melt of polymeric carrier and paroxetine free base;

(c) contacting the molten homogeneous melt of polymeric carrier and paroxetine free base with at least one equivalent of dry hydrogen chloride to form pharmaceutically acceptable noncrystalline paroxetine hydrogen chloride anhydrate in the molten homogeneous melt; and (d) cooling the molten homogeneous melt to form a water soluble solid state dispersion.

22. A process for preparing a water soluble solid state dispersion of paroxetine and a pharmaceutically acceptable polymeric carrier, which process comprises:

(a) contacting a polyethylene glycol with paroxetine free base to form an intimate mixture, wherein the ratio by weight of polyethylene glycol to paroxetine free base is in the range of about 4:1 to about 1:1;

(b) heating the mixture to form a molten homogeneous melt of polyethylene glycol and paroxetine free base;

(c) contacting the molten homogeneous melt of polyethylene glycol and paroxetine free base with at least one equivalent of dry hydrogen chloride to form pharmaceutically acceptable noncrystalline paroxetine hydrogen chloride anhydrate in the molten homogeneous melt; and (d) cooling the molten homogeneous melt to form a water soluble solid state dispersion.

23. A solid state dispersion comprising a pharmaceutically acceptable polymeric carrier and noncrystalline paroxetine salt anhydrate.

24. A pharmaceutical composition comprising a solid state dispersion of claim 23 and one or mote pharmaceutically acceptable excipients.

25. A pharmaceutical composition comprising a solid state dispersion of claim 20 and one or more pharmaceutically acceptable excipients.

26. A method of treating depression in a warm-blooded animal comprising administering to said animal a solid state dispersion as defined in claim 23, the amount of paroxetine hydrochloride in said dispersion being effective for treating depression.

27. A method of treating depression in a warm-blooded animal comprising administering to said animal a solid state dispersion as defined in claim 20, the amount of paroxetine hydrochloride in said dispersion being effective for treating depression.

* * * * *